(12) United States Patent
Goldenberg et al.

(10) Patent No.: US 6,432,449 B1
(45) Date of Patent: Aug. 13, 2002

(54) BIODEGRADABLE SUSTAINED-RELEASE ALGINATE GELS

(75) Inventors: Merrill Seymour Goldenberg; Jian Hua Gu, both of Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/080,832

(22) Filed: May 18, 1998

(51) Int. Cl.[7] .......................... A61K 9/10; A61K 47/36; A61P 3/04
(52) U.S. Cl. .................. 424/486; 424/426; 514/944; 514/909; 514/779
(58) Field of Search .................. 424/484, 429–86, 424/488, 426; 514/944, 909, 779

(56) References Cited

U.S. PATENT DOCUMENTS

| 3,640,741 | A | * | 2/1972 | Etes |
| 5,147,861 | A | * | 9/1992 | della Valle et al. |
| 5,773,416 | A | * | 6/1998 | Chehab |
| 5,831,017 | A | * | 11/1998 | Hoffmann |
| 6,036,978 | A | * | 3/2000 | Gombotz et al. |

* cited by examiner

*Primary Examiner*—Edward J. Webman
(74) *Attorney, Agent, or Firm*—Craig A. Crandall; Ron K. Levy; Steven M. Odre

(57) ABSTRACT

The present invention relates to sustained-release formulations using biodegradable alginate delayed gels or particles and methods thereof.

12 Claims, No Drawings

BIODEGRADABLE SUSTAINED-RELEASE ALGINATE GELS

FIELD OF THE INVENTION

The present invention relates to sustained-release formulations using biodegradable alginate gel beads and/or delayed gels and methods thereof.

BACKGROUND OF THE INVENTION

With the advances in genetic and cell engineering technologies, the availability of recombinant proteins has engendered advances in the use of proteins as medicaments for therapeutic applications. Many illnesses or conditions treated with pharmaceutical proteins require sustained protein levels to achieve the most effective therapeutic result. However, as with most protein pharmaceuticals, the generally short biological half-life requires frequent administration. These repeated injections are given at various intervals which result in fluctuating medication levels at a significant physical and monetary burden on the patients. Since many conditions respond better to controlled levels of a pharmaceutical, a need exists for controlled release of a medicament to provide longer periods of consistent release. Such sustained-release medicaments would provide the patient with not only enhanced prophylactic, therapeutic or diagnostic effects, but also a decrease in the frequency of injections as well as in overall costs.

Current attempts to sustain medication levels in humans or animals between doses have included the use of biodegradable polymers as matrices to control medicament release. For example, Great Britain Patent No. 1,388,580 discloses the use of hydrogels for sustained-release of insulin. U.S. Pat. No. 4,789,550 discloses the use of polylysine coated alginate microcapsules for delivery of protein by encapsulating living cells. Sustained-release attempts have also utilized anionic or cationic polymer compositions surrounded by ionic polymers of the opposite charge for encapsulating cells capable of producing biologically active compositions; U.S. Pat. No. 4,744,933. Likewise, multiple coats of anionic or cationic cross-linking polymers have also been disclosed as means for obtaining controlled release; U.S. Pat. Nos. 4,690,682 and 4,789,516. In addition, further attempts disclose the use of alginates alone, or alginates coated with other biodegradable polymers, for controlled release of polypeptide compositions or cation precipitates thereof; PCT WO 96/00081, PCT WO 95/29664 and PCT WO 96/03116.

These attempts, however, have provided insufficient means for obtaining sustained-release delivery of desired protein pharmaceuticals. It is generally known that the use of certain biodegradable polymers, e.g., polylactide co-glycolide, under in vivo conditions, exhibit high initial bursts of medicament release; Johnson, O. et al., Nature Med., 2(7): 795 (1996). Furthermore, it is generally known that proteins used with current forms of sustained-release preparations can undergo denaturation and lose their bioactivity upon exposure to the encapsulating agents. Such preparations use organic solvents which can have deleterious effects on the protein of choice. Finally, as discussed below, use of alginate alone has not provided the desired controlled protein release necessary for effective therapeutic results.

In general, alginates are well known, naturally occurring, anionic, polysaccharides comprised of 1,4-linked-β-D-mannuronic acid and α-L-guluronic acid; Smidsrod, O. et al., Trends in Biotechnol., 8: 71–78 (1990); Aslani, P. et al., J. Microencapsulation, 13(5): 601–614 (1996). Alginates typically vary from 70% mannuronic acid and 30% guluronic acid, to 30% mannuronic acid and 70% guluronic acid; Smidsrod, supra. Alginic acid is water insoluble whereas salts formed with monovalent ions like sodium, potassium and ammonium are water soluble; McDowell, R. H., "Properties of Alginates" (London, Alginate Industries Ltd, 4th edition 1977). Polyvalent cations are known to react with alginates and to spontaneously form gels.

Alginates have a wide variety of applications such as food additives, adhesives, pharmaceutical tablets and wound dressings. Alginates have also been recommended for protein separation techniques. For example, Gray, C. J. et al., in Biotechnology and Bioengineering, 31: 607–612 (1988) entrapped insulin in zinc/calcium alginate gels for separation of insulin from other serum proteins.

Alginate matrices have also been well documented for drug delivery systems; see for example, U.S. Pat. No. 4,695,463 which discloses an alginate based chewing gum delivery system and pharmaceutical preparations. Alginate beads have been used for controlled release of various proteins such as: tumor necrosis factor receptor in cation-alginate beads coated with polycations; Wee, S. F, Proceed. Intern. Symp. Control. Rel. Bioact. Mater., 21: 730–31 (1994); transforming growth factor encapsulated in alginate beads; Puolakkainen, P. A. et al., Gastroenterology, 107: 1319–1326 (1994); angiogenic factors entrapped in calcium-alginate beads; Downs, E. C. et al., J. of Cellular Physiology, 152: 422–429 (1992); albumin entrapped in chitosan-alginate microcapsules; Polk, A. et al., J. Pharmaceutical Sciences, 83(2): 178–185 (1994); chitosan-calcium alginate beads coated with polymers; Okhamafe, A. O. et al., J. Microencapsul., 13(5): 497–508 (1996); hemoglobulin encapsulated with chitosan-calcium alginate beads; Huguet, M. L. et al., J. Applied Polymer Science, 51: 1427–1432 (1994), Huguet, M. L. et al., Process Biochemistry, 31: 745–751 (1996); and interleukin-2 encapsulated in alginate-chitosan microspheres; Liu, L. S. et al., Proceed. Intern. Symp. Control. Rel. Bioact. Mater, 22: 542–543 (1995).

Systems using alginate gel beads, or alginate/calcium gel beads, to entrap proteins suffer from lack of any sustained-release effect due to rapid release of the protein from the alginate beads; Liu, L. et al., J. Control. Rel., 43: 65–74 (1997). To avoid such rapid release, a number of the above systems attempt to use polycation polymer coatings (e.g., polylysine, chitosan) to retard the release of the protein alginate beads; See, e.g., Wheatley, M. A. et al., J. Applied Polymer Science, 43: 2123–2135 (1991); Wee, S. F. et al. supra; Liu, L. S. et al. supra; Wee, S. F. et al., Controlled Release Society, 22: 566–567 (1995) and Lim, et al. supra.

Polycations, such as polylysine, are positively charged polyelectrolytes which interact with the negatively charged alginate molecules to form a polyelectrolyte complexes that act as diffusion barriers on the bead surface. Problems can occur with the use of polycations in that: (1) such formulations maybe cytotoxic due to the polycations; Huguet, M. L. et al., supra; Zimmermann, Ulrich, Electrophoresis, 13: 269 (1992); Bergmann, P. et al., Clincial Science, 67: 35 (1984); (2) polycations are prone to oxidation; (3) beads with polycation coatings tend not to be erodible and build up in the body; (4) such formulations are made via laborious coating procedures which include multiple coatings of the polycation polylysine; Padol, et al., Proceed. Intern. Symp. Control. Rel. Bioact. Mater, 2: 216 (1986) and (5) ionic interactions between the protein and the polycations can result in loss of protein activity or cause protein instability.

Francesco et al., U.S. Pat. No. 5,336,668 (and references cited therein) describe total and partial esters of alginic acid, made by different processes, and possessing interesting pharmaceutical qualities. It is described how the alginic esters could be utilized as biodegradable plastic materials for medical-surgical use; as additives for a wide range of polymeric materials; or used in the preparation of various medicaments. Potential use the esterified alginates in sustained release formulations is not discussed nor are esterified alginate hydrogels described.

Nightlinger et al., Proceed. Inter. Symp. Control. Rel. Bioact. Mater., 22: 738–739 (1995) describe esterified hyaluronic acid (HA) microspheres having controlled release capabilities. The references generally addresses the different degradation rates for their HA derivatives and describe how the ester "breaks off" to liberate the alcohol and HA moieties. There is no discussion relating how or whether the HA backbone itself breaks down into lower molecular weight polymer units.

In order for a polysaccharide based sustained delivery system to be useful, the polysaccharide must be biodegradable into non-toxic products. It has been found that certain alginate gel systems, while effective in providing sustained release of drug, results in a "bump" (or nodule) at the site of injection due to the very slow dissipation of the gel. In a therapeutic setting involving low doses of drug and infrequent injections, this might not be a major problem. However, in a therapeutic setting involving high doses of drug and more frequent injections, this effect could be prohibitive. A means for increasing the dissipation rate of the alginate gel from the injection site must be developed.

There is thus still a need to develop pharmaceutical formulations which achieve a more versatile and effective means of sustained-release for clinical applications. Numerous recombinant or natural proteins could benefit from constant long term release and thereby provide more effective clinical results.

The present invention provides such advances. Pharmaceutical compositions using the biodegradable alginate gel particles or gels of the present invention are capable of providing increased bioavailability, protein protection, decreased degradation and slow release with increased protein stability and potency. Also, pharmaceutical compositions of the present invention provide a simple, rapid and inexpensive means of controlled recombinant protein release for effective prophylactic, therapeutic or diagnostic results.

SUMMARY OF THE INVENTION

The present invention grew out of studies using unmodified alginate (a class of anionic polysaccharides) hydrogels for the sustained release of proteins. These protein-containing unmodified alginate hydrogels (see copending U.S. application Ser. No. 08/857,973 and 08/912,902) are formed in a time-delayed manner whereby the materials can be filled in a syringe and left to later gel in the same syringe; these gels are found to be injectable. After a single subcutaneous injection in rodent models evidence of many days of sustained protein is observed; however, a perceptible bump or nodule remains at the injection site for long periods of time with little change in its size. This bump consists of the water-filled alginate hydrogel and the size of the bump is a function of the volume of gel that is injected. Gel beads also remain at the injection site.

The present invention thus relates to a novel class of biodegradable biocompatible polysaccharide hydrogels, e.g. alginate ester hydrogels, for the sustained release of therapeutic proteins. Unexpectedly, the alginate ester hydrogels, in addition to having the gelation, injectability and sustained release properties of the unmodified alginates, did not leave a bump at the injection site that is, the alginate ester hydrogels are biodegradable or erodible and are gradually resorbed into the surrounding tissues with little injection site reaction.

The compositions of the present invention comprise alginate esters or their derivatives ionically crosslinked in a hydrogel (water-containing) matrix containing a therapeutic agent such as a protein.

The present invention further relates to a method of producing biodegradable sustained release compositions.

The present invention further relates to the use of the ester alginate materials in liquid mixtures for time delay gelation in the body.

The present invention further relates to compositions wherein the: alginate ester hydrogels are in the form of beads or microspheres for the sustained release of active agents preferably therapeutic proteins.

In one embodiment of the present invention the alginate ester hydrogels provide compositions for application at target sites in the body of a patient.

These compositions are useful: for preventing or inhibiting the formation of tissue adhesions following surgery and traumatic injury; for supplementing tissues especially for filling soft and hard tissues; to fill a confined space with a resorbable material; as a scaffold for tissue growth; and as a wound dressing.

In another embodiment the alginate ester hydrogels provide active gent containing devices for implantation in the body whereby the agent can be either bound or unbound to the alginate polymer.

In another embodiment the alginate ester hydrogel compositions of the present invention provide a method for improving the bioavailability of the active agent in the composition.

Finally, the alginate ester hydrogel compositions of the present invention further provide a method for obtaining a substantially constant blood level over time in the patient.

DETAILED DESCRIPTION OF THE INVENTION

Compositions

Hydrophilic polymers including alginates and derivatives thereof, can,be obtained from various commercial, natural or synthetic sources well known in the art. As used herein, the term hydrophilic polymer refers to water soluble polymers or polymers having affinity for absorbing water. Hydrophilic polymers are well known to one skilled in the art. These include but are not limited to polyanions, including anionic polysaccharides such as alginate, carboxymethyl amylose, polyacrylic acid salts, polymethacrylic acid salts, ethylene maleic anhydride copolymer (half ester), carboxymethyl cellulose, dextran sulfate, heparin, carboxymethyl dextran, carboxy cellulose, 2,3-dicarboxycellulose, tricarboxycellulose, carboxy gum arabic, carboxy carrageenan, pectin, carboxy pectin, carboxy tragacanth gum, carboxy xanthan gum, pentosan polysulfate, carboxy starch, carboxymethyl chitin/chitosan, curdlan, inositol hexasulfate, b-cyclodextrin sulfate, hyaluronic acid, chondroitin-6-sulfate, dermatan sulfate, heparin sulfate, carboxymethyl starch, carrageenan, polygalacturonate, carboxy guar gum, polyphosphate, polyaldehydo-carbonic acid, poly-1-hydroxy-1-sulfonate-propen-2, copolystyrene maleic acid, agarose, mesoglycan, sulfopropylated polyvinyl alcohols, cellulose sulfate, protamine sulfate, phospho guar gum, polyglutamic acid, polyaspartic acid, polyamino acids, derivatives or combinations thereof. One skilled in the art will appreciate other various hydrophilic polymers that are within the scope of the present invention.

Likewise, bound polyvalent metal ions can be obtained from various commercial, natural or synthetic sources which are well known in the art. In particular, the metal ions can include but are not limited to aluminum, barium, calcium, iron, manganese magnesium, strontium and zinc. Preferably the metal ions are calcium and zinc or the salts thereof, like zinc acetate, calcium acetate or chloride salts. Water soluble small molecules and salts can also be used such as ammonium sulfate, acetone, ethanol and glycerol.

Alcohols of the aliphatic series for use as esterifying components of the carboxy groups of alginic acid according to the present invention are, for example, those with a maximum of 34 carbon atoms, which may be saturated or unsaturated and which may possibly also be substituted by other free or functionally modified groups, such as amino, hydroxy, aldehydo, keto, mercapto, carboxy groups or by groups deriving from the same, such as hydrocarbyl or dihydrocarbylamino (hereafter the term "hydrocarbyl" should be taken to mean not only monovalent radicals of hydrocarbons such as the $C_nH_{2n+1}$ type but also bivalent or trivalent radicals, such as "alkylenes" —$C_nH_{2-}$ or "alkylidenes" =$C_nH_{2n}$), ether or ester groups, acetal or ketal groups, thio-ether or thioester groups and esterified carboxy groups or carbamidic or carbamidic groups substituted by one or two hydroxy groups, by nitrile groups or by halogens.

In the above groups containing hydrocarbyl radicals these are preferably lower aliphatic radicals, such as heteroatoms, such as oxygen, nitrogen and sulfur. Preference is given to alcohols substituted with one or two of the aforesaid function groups.

Alcohols of the above group to be used preferentially within the terms of the present invention are those with a maximum of 12 and especially with a maximum of 6 carbon atoms and in which the hydrocarbyl radicals in the above mentioned amino, ether, ester, thioether, thioester, acetal, ketal groups representing alkyl groups with a maximum of 4 carbon atoms, and also in the esterified carboxy or substituted carbamidic groups the hydrocarbyl groups are alkyls with the same number of carbon atoms, and in which the amino or carbamidic groups may be alkyleneamino or alkylenecarbamidic groups with a maximum of 8 carbon atoms. Of these alcohols those to be mentioned first and foremost are the saturated and unsubstituted ones such as methyl, ethyl, propyl, isopropyl alcohols, n-butyl alcohol, isobutyl, tert-butyl alcohols, amyl, pentyl, hexyl, octyl, nonyl, and dodecyl alcohols and above all those with a linear chain such as n-octyl or n-dodecyl alcohols. Of the substituted alcohols of this group the bivalent alcohols should be listed, such as ethyleneglycol, propylene glycol or butylene glycol, the trivalent alcohols such as glycerin, aldehydo alcohols such as tartronic alcohol, carboxy alcohols such as lactic acids, for example alpha-oxypropionic acid, glycolic acid, malic acid, tartaric acids, citric acid, aminoalcohols, such as aminoethanol, aminopropanol, n-aminobutanol and their dimethyl and diethyl derivatives in the aminic function, choline, pyrrolidinylethanol, piperidinylethanol, piperazinylethanol and the corresponding derivatives of n-propyl or n-butyl alcohols, monothioethyleneglycol or its alkyl derivatives, for example the ethylderivative in the mercapto function.

Of the higher saturated aliphatic alcohols, those worthy of special mention are for example cetyl alcohol and myristyl alcohol, but especially important for the purposes of the present invention are the higher unsaturated alcohols with one or two double bonds, such as especially those contained in many essential oils and having an affinity with terpenes such as citronellol, geraniol, nerol, nerolidol, linalool, farnesol, phytol.

Of the lower unsaturated alcohols consideration should be given to propargyl alcohol.

Of the aliphatic alcohols those to be mentioned above all are those with only one benzene residue and in which the aliphatic chain has a maximum of 4 carbon atoms, in which also the benzene residue may be substituted by between 1 and 3 methyl or hydroxy groups or by halogen atoms,, especially chlorine, bromine or iodine and in which the aliphatic chain may be substituted by one or more functional groups selected from the group consisting of free amino groups or mono- or dimethyl groups or by pyrrolidine or piperidine groups. Of these alcohols, benzyl alcohol and phenethyl alcohol are especially preferred. The alcohols of the cycloaliphatic or aliphatic ccycloaliphatic series may derive from mono or polycyclic hydrocarbons and may have a maximum of 34 carbon atoms. Of the alcohols derived from cyclic monoanular hydrocarbons special mention should be given to those with a maximum of 12 carbon atoms, with rings containing preferably between 5 and 7 carbon atoms, possibly substituted for example by between one and three lower alkyl groups, such as methyl, ethyl, propyl or isopropyl groups. Specific alcohols of this group are cyclohexanol, cyclohexanediol, 1,2,3-cyclohexanetriol and 1,3,5-cyclohexanetriol (phloroglucitol), inositol, the alcohols deriving from p-menthane such as carvomenthol menthol, alpha and gamma-terpineol 1-terpineol alcohols known as "terpineol", 1,4-and 1,8-terpin. Alcohols deriving from hydrocarbons with condensed rings are, for example, those of the thujane, pinane, campbane groups, particularly thujanol, sabinol pinol hydrate, D and L-borneol and D and L-isoborneol.

Also to be included are alcohols derived from the esterification reaction of epoxy-containing compounds with alginates (See e.g., U.S. Pat. No. 2,463,824 and U.S. Pat. No. 2,426,125).

The total and partial ester group containing polyanions of the present invention are generally acidic polysaccharides where the glycosidic oxygen is attached beta to the carbonyl carbon of the ester. While not being bound to any specific mechanism, this arrangement of the moieties allows the breakdown of the polymer chain by a beta-elimination mechanism which can occur under physiological conditions.

Alginic acid esters of the present invention are comprised of mannuronic acid residues (m-COOH or m-COO anion) and guluronic acid residues (g-COOH or g-COO anion) joined together by glycosidic ether oxygen linkages of the following general formula I:

  I where:
M is a mannuronic acid residue, m-COOH or m-COO anion;
M' is a mannuronic acid ester residue, m-COOR1;
G is a guluronic acid residue, g-COOH or g-COO anion;
G' is a guluronic acid ester residue, g-COOR2;
A represents non-g or non-m chain units, such as sugars, sugar oxidation products, or aliphatic, aromatic, araliphatic, alaromatic, cycloaliphatic radicals which can be substituted and interrupted by heteroatoms linked within or at the chain ends;

n1, n2, n3, n4 and n5 are integers representing the average relative number of incorporated units;

R1 and R2 are independently aliphatic, aromatic, araliphatic, alaromatic, cycloaliphatic radicals which can be substituted and interrupted by heteroatoms;

and derivatives (e.g. where the hydroxy groups are acetylated and are reacted with isocyanates) and pharmaceutically acceptable salts thereof.

In the esters of the present invention, it is desirable that R1=R2=aliphatic or alaromatic and further that $100(n2+n4)/(n1+n2+n3+n4)$ is from 1–99 mol %, preferably 5–50 mol %, more preferably 6–30 mol %, still more preferably 6–15 mol % and most preferably 7–12 mol % and $100n5/(n1+n2+n3+n4+n5)$ is preferably less than 10 mol %.

In the partial esters of the invention the non-esterified carboxy groups may be kept free or may be salified. The bases for the formation of these salts are chosen according to the ultimate end use of the product. Inorganic salts maybe formed from alkaline metals, such as potassium and in particular sodium and ammonium, or deriving from alkaline earth metals such as calcium or magnesium or aluminum salts. Of particular interest are the salts with organic bases, especially azotized bases and, therefore, aliphatic, araliphatic, cycloaliphatic or heterocyclic amines. These ammonium salts may derive from therapeutically acceptable amines or nontoxic but therapeutically inactive amines, or from amines with a therapeutic action. Of the first type, preferred are aliphatic amines, for example mono-, di- and tri-alkylamines with alkyl groups with a maximum of 8 carbon atoms or arylalkylamines with the same number of carbon atoms in the aliphaic part and where aryl means a benzene group possibly substituted by between 1 and 3 methyl groups or halogen atoms or hydroxy groups. The biologically inactive bases for the formation of the salts may also be cyclic., such as monocyclic alkyleneamines with cycles of between 4 and 6 carbon atoms, possibly interrupted in their cycle by heteroatoms chosen from the group formed by nitrogen, oxygen and sulphur, such as piperazine or morpholine, or may be substituted, for example by amino or hydroxy functions such as aminoethanol, ethylenediamol, ethylenediamine, ephedrine or choline.

The degree of and type of esterification can be controlled by synthetic methods known in the art. Preferably, the alginate esters are prepared by treatment of the quaternary ammonium salts of alginic acid with conventional alkylating agents in an aprotic organic solvent such as dimethyl sulfoxide. The resultant esters are preferably the esters of monovalent alcohols such as lower alkyl such as ethyl or aralkyl such as benzyl or their mixtures. One can also form esters by the reaction of alginic acid with oxirane or epoxy containing compounds such as ethylene or propylene oxide.

It is also possible to form quaternary ammonium salts of partial esters, for example the salts of tetraalkylammonium with the above said number of carbonatoms and preferably salts of this type in which the fourth alkyl group has between 1 and 4 carbon atoms, for example a methyl group.

The degree of esterification (expressed in mol %) of the alginate is related to the desired disappearance rate of the gel in the patient tissue. This disappearance rate of the gel is generally related to the desired release rate of the active agent from the gel that is over a period of 5 years or less, usually 2 days to 270 days, more usually 2 days to 180 days, more usually 2 days to 90 days. The degree of esterification (DE) is from 1 mol % to 99 mol %, preferably from 5 mol % to 50 mol %, more preferably from 6 mol % to 30 mol %, more preferably from 6 mol % to mol %, more preferably from 7 mol % to 12 mol %.

As used herein, the term buffer or buffer solution refers to use of inorganic or organic acids or a combination thereof to prepare a buffer solution as known in the art. Inorganic acids within the scope of the present invention include hydrogen halide (e.g., hydrochloric acid), phosphoric, nitric or sulfuric. Other inorganic acids would be well known to one skilled in the art and are contemplated herein. Organic acids within the scope of the invention include aliphatic carboxylic acids and aromatic acids such as formic, carbonic, acetic, propionic, butyric, valeric, caproic, acrylic, malonic, succinic, glutaric, adipic, maleic, fumaric, glycine or phenol sulfonic. Other organic acids would be well known to one skilled in the art.

As used herein, biologically active agents refers to recombinant or naturally occurring proteins, whether human or animal, useful for prophylactic, therapeutic or diagnostic application, as well as non-protein based agents such as small molecules. The biologically active agent can be natural, synthetic, semi-synthetic or derivatives thereof. The biologically active agents of the present invention must be precipitable. A wide range of biologically active agents are contemplated. These include but are not limited to hormones, cytokines, hematopoietic factors, growth factors, antiobesity factors, trophic factors, anti-inflammatory factors, and enzymes (see also U.S. Pat. No. 4,695,463 for additional examples of useful biologically active agents). One skilled in the art will readily be able to adapt a desired biologically active agent to the compositions of present invention.

Such proteins would include but are not limited to interferons (see, U.S. Pat. Nos. 5,372,808, 5,541,293 4,897,471, and 4,695,623 hereby incorporated by reference including drawings), interleukins (see, U.S. Pat. No. 5,075,222, hereby incorporated by reference including drawings), erythropoietins (see, U.S. Pat. Nos. 4,703,008, 5,441,868, 5,618,698 5,547,933, and 5,621,080 hereby incorporated by reference including drawings), granulocyte-colony stimulating factors (see, U.S. Pat. Nos. 4,810,643, 4,999,291, 5,581,476, 5,582,823, and PCT Publication No. 94/17185, hereby incorporated by reference including drawings), stem cell factor (PCT Publication Nos. 91/05795, 92/17505 and 95/17206, hereby incorporated by reference including drawings), and the OB protein (see PCT publication Nos. 96/40912, 96/05309, 97/00128, 97/01010 and 97/06816 hereby incorporated by reference including figures). In addition, biologically active agents can also include but are not limited to anti-obesity related products, insulin, gastrin, prolactin, adrenocorticotropic hormone (ACTH), thyroid stimulating hormone (TSH), luteinizing hormone (LH), follicle stimulating-hormone (FSH), human chorionic gonadotropin (HCG), motilin, interferons (alpha, beta, gamma), interleukins (IL-1 to IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), insulin-like growth factors (IGFs), macrophage colony stimulating factor (M-CSF), granulocyte macrophage colony stimulating factor (GM-CSF), megakeratinocyte derived growth factor (MGDF), thrombopoietin, platelet-derived growth factor (PGDF), colony simulating growth factors (CSFs), bone morphogenetic protein (BMP), superoxide dismutase (SOD), tissue plasminogen activator (TPA), urokinase, streptokinase and kallikrein. The term proteins, as used herein, includes peptides, polypeptides, consensus molecules, analogs, derivatives or combinations thereof.

Derivatives of biologically active agents may include the attachment of one or more chemical moieties to the protein moiety. Chemical modification of biologically active agents has been found to provide additional advantages under certain circumstances, such as increasing the stability and circulation time of the therapeutic protein and decreasing immunogenicity. One skilled in the art will be able to select the desired chemical modification based on the desired dosage, circulation time, resistance to proteolysis, therapeutic uses and other considerations.

As used herein, biodegradability refers to the breakdown of the molecular weight of a particular polymer into a smaller number of units in the chain, i.e., breakdown into lower molecular weight units. Biodegradble gel refers to the dissipation of the gel in the environment of use, where the idssipation is contingent on the breakdown of the molecular weight of the constituent polymers, resulting in fewer units in the polymer chain.

Complexes

The proteins, analog or derivative may be administered complexed to a binding composition. Such binding composition may have the effect of prolonging the circulation time of the protein, analog or derivative or enhancing the activity of the biologically active agent. Such composition may be a protein (or synonymously, peptide), derivative, analog or combination. For example, a binding protein for the OB protein is OB protein receptor or portion thereof, such as a soluble portion thereof. Other binding proteins may be ascertained by examining OB protein, or the protein of choice, in serum, or be empirically screening for the presence of binding. Such binding will typically not interfere with the ability of OB protein or analog or derivative to bind to endogenous OB protein receptor and/or effect signal transduction. In addition to the OB protein, binding complexes will also be applicable to other therapeutic proteins of the present invention as well. Those well skilled in the art will be able to ascertain appropriate binding proteins for use with the present invention.

Likewise, precipitating agents used to precipitate the biologically active agent can be obtained from various commercial, natural or synthetic sources which are well known in the art. Precipitating agents include but are not limited to polyvalent metal ions or their salts such as acetates, citrates, chlorides, carbonates, hydroxides, oxalates, tartrates or hydroxides thereof, acids or water soluble polymers. In particular, the metal ions can include but are not limited to aluminum, barium, calcium, iron, manganese magnesium, strontium and zinc. Preferably the metal ion is zinc or the salts thereof, like acetate chloride salts. Water soluble small molecules and salts can also be used such as ammonium sulfate, acetone, ethanol and glycerol.

As for water soluble polymers these include but are not limited to polyethylene glycol, ethylene glycol/propylene glycol copolymers, carboxylmethylcellulose, dextran, polyvinyl alcohol, polyvinyl pyrolidone, poly-1, 3-dioxolane, poly-1,3,6-trioxane, ethylene/maleic anhydride copolymers, polyaminoacids, dextran, poly (n-vinyl pyrolidone) polyethylene glycol, propylene glycol homopolymers, polypropylene oxide/ethylene oxide copolymers, polyoxyethylated polyols, polyvinyl alcohol succinate, glycerine, ethylene oxides, propylene oxides, poloxamers, alkoxylated copolymers, water soluble polyanions, derivatives or combinations thereof. The water soluble polymer may be of any molecular weight, and may be branched or unbranched. For example, the preferred molecular weight of polyethylene glycol is between about 700 Da and about 100 kDa for ease in handling and efficiency of precipitation.

Other sizes and types of precipitating agents, may be used, depending on the desired therapeutic profile (e.g., the duration of sustained-release desired, the effects, if any on biological activity, the ease in handling, the degree or lack of antigenicity and other known effects of a desired precipitating agent to a therapeutic protein or analog). One skilled in the art will appreciate other precipitating agents that are within the scope of the invention.

In addition, the compositions of the present invention may also include extra excipients necessary to stabilize the biologically active agent and/or the hydrophilic polymer. These can be contained in the buffer and may include but are not limited to preservatives.

Pharmaceutical Compositions

The sustained-release pharmaceutical compositions of the present invention may be administered by oral (e.g., capsules such as hard capsules and soft capsules, solid preparations such as granules, tablets, pills, troches or lozenges, cachets, pellets, powder and lyophilized forms, liquid preparations such as suspensions) and non-oral preparations (e.g., intramuscular, subcutaneous, transdermal, visceral, IV (intravenous), IP (intraperitoneal), intraarterial, intrathecal, intracapsular, intraorbital, injectable, pulmonary, nasal, rectal, and uterine-transmucosal preparations).

In general, comprehended by the invention are sustained-release pharmaceutical compositions comprising effective amounts of protein, or derivative products, with the sustained-release compositions of the invention together with pharmaceutically acceptable diluents, preservatives, solubilizers, emulsifiers, adjuvants and/or carriers needed for administration. See PCT 97/01331 hereby incorporated by reference. The optimal pharmaceutical formulation for a desired biologically active agent will be determined by one skilled in the art depending upon the route of administration and desired dosage. Exemplary pharmaceutical compositions are disclosed in Remington's Pharmaceutical Sciences (Mack Publishing Co., 18th Ed., Easton, Pa., pgs. 1435–1712 (1990)).

Due to the thixotropic nature of the delayed gel formulation, syringes can be used to administer subcutaneously. The composition may be gelled in a syringe for later injection. This gelation can be performed in a time-delayed manner. The timing is controlled by the judicious adjustment of the quantity of the gelling agent and the proton donor in the mixture, if needed. Such a preparation would be used for later re-gelation in the body after injection. The term thixotropic as used herein refers to the viscosity of the gel mixture which decreases under pressure, e.g., from the syringe plunger, at which point the mixture can flow, e.g., through the syringe needle, and then reform a gel at the injection site.

The concept of delayed gelation can also be applied to filling a syringe where a sustained-release gel composition is filled in a syringe and at a preset time gels in the syringe, e.g., from a few minutes to many hours after filling. This avoids the problem of filling a syringe with material that has already gelled. These prefilled syringes can be stored for later injection into patients.

Components that may be needed for administration include diluents of various buffer content (e.g., Tris-HCl, acetate), pH and ionic strength; additives such as surfactants and solubilizing agents (e.g., Tween 80, HCO-60, Polysorbate 80), anti-oxidants (e.g., ascorbic acid, glutathione, sodium metabisulfite), additional polysaccharides (e.g., carboxymethylcellulose, sodium alginate, sodium hyaluronate, protamine sulfate, polyethylene glycol), preservatives (e.g., Thimersol, benzyl alcohol, methyl paraben, propyl paraben) and building substances (e.g., lactose, mannitol); incorporation of the material into particulate preparations of polymeric compounds such as polylactic/polyglycolic acid polymers or copolymers, etc. or combined with liposomes. Hylauronic acid may also be used as an administration component and this may have the effect of promoting even further the sustained duration in the circulation. Additionally, sustained-release compositions of the present invention may also be dispersed with oils (e.g., sesame oil, corn oil, vegetable), or a mixture thereof with a phospholipid (e.g., lecitin), or medium chain fatty acid triglycerides (e.g., Miglyol 812) to provide an oily suspension. The compositions of the present invention may also be dispersed with dispersing agents such as water-soluble polysaccharides (e.g., mannitol, lactose, glucose, starches), hyaluronic acid, glycine, fibrin, collagen and inorganic salts (e.g., sodium chloride).

In addition, also contemplated for use in the administration of the sustained-release compositions of the present invention are mechanical devices designed for pulmonary delivery of therapeutic products, including but not limited to nebulizers, metered dose inhalers, and powder inhalers, all of which are familiar to those skilled in the art.

The administration components may influence the physical state, stability, rate of in vivo release, and rate of in vivo clearance of the present proteins and derivatives. One skilled in the art will appreciate the appropriate administration components and/or the appropriate mechanical devices to use depending on the therapeutic use, route of administration, desired dosage, circulation time, resistance to proteolysis, protein stability and other considerations.

Methods of Use

Therapeutic

Therapeutic uses depend on the biologically active agent used. One skilled in the art will readily be able to adapt a desired biologically active agent to the present invention for its intended therapeutic uses. Therapeutic uses for such agents are set forth in greater detail in the following publications hereby incorporated by reference including drawings. Therapeutic uses include but are not limited to uses for proteins like interferons (see, U.S. Pat. Nos. 5,372,808, 5,541,293 4,897,471, and 4,695,623 hereby incorporated by reference including drawings), interleukins (see, U.S. Pat. No. 5,075,222, hereby incorporated by reference including drawings), erythropoietins (see, U.S. Pat. Nos. 4,703,008, 5,441,868, 5,618,698 5,547,933, and 5,621,080 hereby incorporated by reference including drawings), granulocyte-colony stimulating factors (see, U.S. Pat. Nos. 4,999,291, 5,581,476, 5,582,823, 4,810,643 and PCT Publication No. 94/17185, hereby incorporated by reference including drawings), stem cell factor (PCT Publication Nos. 91/05795, 92/17505 and 95/7206, hereby incorporated by reference including drawings), and the OB protein (see PCT publication Nos. 96/40912, 96/05309, 97/00128, 97/01010 and 97/06816 hereby incorporated by reference including figures).

In addition, therapeutic uses of the present invention include uses of biologically active agents including but not limited to anti-obesity related products, insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferons (alpha, beta, gamma), interluekins (IL-1 to IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), insulin-like growth factors (IGFs), macrophage colony stimulating factor (M-CSF), granulocyte macrophage colony stimulating factor (GM-CSF), megakeratinocyte derived growth factor (MGDF), thrombopoietin, platelet-derived growth factor (PGDF), colony simulating growth factors (CSFs), bone morphogenetic protein (BMP), superoxide dismutase (SOD), tissue plasminogen activator (TPA), urokinase, streptokinase and kallikrein. The term proteins, as used herein, includes peptides, polypeptides, consensus molecules, analogs, derivatives or combinations thereof. In addition, the present compositions may also be used for manufacture of one or more medicaments for treatment or amelioration of the conditions the biologically active agent is intended to treat.

By way of example, therapeutic uses oxygenation in the blood) and a decrease in bone resorption or osteoporosis may also be achieved in the absence of weight loss.

Combination Therapies

The present compositions and methods may be used in conjunction with other therapies, such as altered diet and exercise. Other medicaments, such as those useful for the treatment of diabetes (e.g., insulin, and possibly amylin), cholesterol and blood pressure lowering medicaments (such as those which reduce blood lipid levels or other cardiovascular medicaments), activity increasing medicaments (e.g., amphetamines), diuretics (for liquid elimination), and appetite suppressants. Such administration may be simultaneous or may be in seriatim. In addition, the present methods may be used in conjunction with surgical procedures, such as cosmetic surgeries designed to alter the overall appearance of a body (e.g., liposuction or laser surgeries designed to reduce body mass, or implant surgeries designed to increase the appearance of body mass). The health benefits of cardiac surgeries, such as bypass surgeries or other surgeries designed to relieve a deleterious condition caused by blockage of blood vessels by fatty deposits, such as arterial plaque, may be increased with concomitant use of the present compositions and methods. Methods to eliminate gall stones, such as ultrasonic or laser methods, may also be used either prior to, during or after a course of the present therapeutic methods. Furthermore, the present methods may be used as an adjunct to surgeries or therapies for broken bones, damaged muscle, or other therapies which would be improved by an increase in lean tissue mass.

Dosages

One skilled in the art will be able to ascertain effective dosages by administration and observing the desired therapeutic effect. The dosage of the sustained-release preparation is the amount necessary to achieve the effective concentration of the biologically active agent in vivo, for a given period of time. The dosage and the preferred administration frequency of the sustained-release preparations varies with the type of the biologically active agent, the desired duration of the release, the target disease, desired administration frequency, the subject animal species and other factors. Preferable, the formulation of the molecule will be such that between about 0.10 µg/kg/day and 100 mg/kg/day will yield the desired therapeutic effect.

The effective dosages may be determined using diagnostic tools over time. By way of example, the present invention provides the dosages of OB protein. For example, a diagnostic for measuring the amount of OB protein in the blood (or plasma or serum) may first be used to determine endogenous levels of OB protein. Such diagnostic tool may be in the form of an antibody assay, such as an antibody sandwich assay. The amount of endogenous OB protein is quantified initially, and a baseline is determined. The therapeutic dosages are determined as the quantification of endogenous and exogenous OB protein (that is, protein, analog or derivative found within the body, either self-produced or administered) is continued over the course of therapy. For example, a relatively high dosage may be needed initially, until therapeutic benefit is seen, and then lower dosages used to maintain the therapeutic benefits.

Materials and Methods

Materials

Alginate in the form of sodium alginate can be found from sources well known in the art. OB protein and GCSF are from Amgen Inc. Other chemicals are from sources well known in the art.

Alginate Hydrogel Particle/Bead Preparation

The preparation of the alginate hydrogel particles and beads, with and without proteins, is described in detail in co-pending U.S. application 08/842,756, hereby incorporated by reference.

Delayed Gel Preparation

The preparation of the delayed alginate hydrogels, with and without proteins, is described in detail in copending U.S. application Ser. Nos. 08/857,973 and 08/912,902, each of which is hereby incorporated by reference.

The following examples are offered to more fully illustrate the invention, but are not to be construed as limiting the scope thereof. In addition, with respects to the above disclosure or the examples below, one skilled in the art will be able to make the necessary changes to the disclosures for large scale production.

EXAMPLE 1

The following example describes the preparation of alginate esters to be used in the present invention.

Preparation A: Tetrabutylammonium(TBA) alginate

A sulfonic acid resin (Bio-Rad, AG MP-50) is converted to the tetrabutylammonium(TBA) form by treatment with tetrabutylammonium hydroxide (Aldrich) using a batch method at room temperature. To a solution of 10 g of sodium salt of alginic acid in 800 ml of distilled water is added 60 ml of sulfonic resin (Bio-Rad, AG MP-50) in the tetrabutylammonium salt form. The mixture is stirred at room temperature for 0.5 hours. The resin is removed by filtration and washed with distilled water. The TBA alginate in the filtrate is isolated by freeze-drying (yield, 16.8 g) and confirmed by $^1$H NMR.

Preparation B: Partial ethyl ester of alginic acid, degree of esterification (DE)=30 mol %.

TBA alginate( 6 g, 14.4 mmol TBA units) is dissolved in 500 ml dimethyl sulfoxide (DMSO) at room temperature. Iodoethane (Aldrich, 673 mg, 4.3 mmol) is then added. The mixture is stirred at 30° C. for 15 hours, then cooled to room temperature. To this solution is slowly added a solution of 2 g NaCl in 20 mL water to completely convert the TBA to the sodium salt. After stirring 15–30 min, the solution is slowly poured into 1500 mL ethyl acetate. The precipitate is collected by filtration and washed three times with acetone/water (8:1 v/v) and three times with acetone, then vacuum dried. The compound is redissolved in distilled water (~100 mL) and the pH adjusted to ~6.5 with 0.2% NaHCO$_3$ at 0° C. The solution is then dialyzed (MW cut-off 8000) overnight against distilled water at 4° C. and then freeze-dried. The yield of the partial ester is 2.8 g and the degree of esterification is 30+/−1% ($^1$H NMR, maleimide as internal standard).

Preparation C: Total and partial ethyl ester of alginic acid, DE=100%, 50%, 20%, 10% and 5%.

The preparation of these compounds is similar to that described in Preparation B except that the amount of iodoethane added is adjusted to arrive at the desired degree of esterification.

Preparation D: Partial propyl, hexyl, octyl and dodecyl esters of alginic acid.

The preparations are similar to that described in Preparations B and C above, but substituting 1-iodopropane, 1-iodohexane, 1-iodooctane or 1-iodododecane for iodoethane respectively.

Preparation E: Partial benzyl ester of alginic acid, DE=30%.

TBA alginate (2.5 g, 5.99 mmol TBA units) is dissolved in ~200 mL DMSO at room temperature. Benzyl bromide (Aldrich, 307 mg, 1.8 mmol) and TBA iodide (Aldrich, 30 mg) are added. The mixture is stirred at 30° C. for 15 hours, and then cooled to room temperature. To this solution is slowly added a solution of 0.6 g NaCl in 10 mL water to completely convert the TBA to the sodium salt. After stirring 15–30 minutes, the solution is slowly poured into 500 mL ethyl acetate. The precipitate is collected by filtration and washed three times with acetone/water (8:1 v/v) and three times with acetone, then vacuum dried. The compound is redissolved in distilled water (~60 mL) and adjusted to pH ~6.5 with 0.2% NaHCO at 0° C., then dialyzed (MW cut-off 8000) overnight against distilled water at 4° C. The yield of the partial ester is 1.3 g and the degree of esterification is 30+/−1% ($^1$H NMR, maleimide as internal standard).

Preparation F: Total and partial benzyl ester of alginic acid with different DE.

The preparation of these compounds is similar to that described in Preparation E except that the amount of benzyl bromide and TBA iodide added are adjusted to arrive at the desired degree of esterfication.

EXAMPLE 2

The following example shows the preparation of a protein drug(Leptin)-containing alginate ethyl ester (DE=15 mol % and 10 mol %) gel and the in vitro sustained release from this gel.

Leptin (100 mg/mL; 10 mM Tris HCl, pH 8.8; pH adjusted from 8.0 to 8.8 with 1M NaOH) and 6% ethyl ester alginate (15 mol %, 10 mM Tris HCl, pH 8.6) are cooled on an ice bath. Leptin (0.5 mL) is added to the 6% ethyl ester alginate (0.18 mL) and the mixture stirred on an ice bath for 10–15 min; the final pH is 8.6–8.8. To this mixture is added a suspension of 1M CaCO$_3$ (16 μL) and the resulting suspension is mixed well. To this suspension is dropwise added, with stirring, a solution of 0.1M ZnCl$_2$ (100 μL); water is then added to bring the volume to 1 mL. The mixture is mixed completely and kept on an ice bath for 10–20 min. Then a solution of 1.68M δ-gluconolactone (Aldrich, 56 μL) is thoroughly stirred into this mixture. The final mixture (50 mg/mL leptin, 1% ethyl ester alginate; 0.1 mL) is cast on the inside of an eppendorf tube and left overnight at 4° C. to gel. After overnight storage, in vitro release is conducted in 10 mM histidine buffer, pH 7.4. The cast gel with 15 mol % degree of esterification exhibits minimal burst and fairly constant leptin release showing 60% released in 6 days. The cast gel with 10 mol % degree of esterification exhibits minimal burst and fairly constant leptin release showing 55% released in 6 days.

EXAMPLE 3

The following example shows the preparation of a protein drug(Leptin)-containing alginate hexyl ester (DE=15 mol % and 10 mol %) gel and the in vitro sustained release from this gel.

This example is performed in a similar manner as that described in Example 2 except that the ethyl ester alginate The hexyl ester alginate gels with 15 mol % and 10 mol % of degree of esterification exhibit minimal burst and exhibits sustained release showing 50% released in 6 days.

EXAMPLE 4

The following example shows the preparation of a protein drug (Zn-Leptin)-containing alginate ethyl ester (DE=15 mol %) gel and the in vitro sustained release from this gel.

To a solution of 4% (w/v) ethyl ester alginate (15 mol %, 0.75 mL) is added 1M Tris HCl pH 8.0 (7.5 $\mu$L), 0.5 M PIPES pH 6.8 (33 $\mu$L) and 0.1 M $ZnCl_2$ (8.5 $\mu$L). The mixture is stirred well. To this solution is added Zn-leptin suspension (100 mg/mL, 675 $\mu$L) and the mixture thoroughly stirred. A suspension of 1M $CaCO_3$ (24 $\mu$L) and a solution of 1.68M d-gluconolactone (70 $\mu$L) are then thoroughly stirred into this mixture. The final mixture (0.1 mL) is cast on the inside of an eppendorf tube and left overnight at 4° C. to gel. After overnight storage in vitro release is conducted in 10 mM histidine buffer, pH 7.4. This cast ethyl ester alginate gel with 15 mol % degree of esterification exhibits little burst and sustained leptin release showing 65% released in 4 days.

EXAMPLE 5

The following example shows the preparation of a protein drug(GCSF)-containing alginate ethyl ester (DE=30 mol %) gel and the in vitro sustained release from this gel.

To a solution of 2.39% ethyl ester alginate (30 mol %, 0.5 mL) is added 0.1M acetate buffer (pH 4.5, 100 $\mu$L), GCSF (104 $\mu$L, 48.2 mg/mL, HCl pH3) and distilled water (246 mL). The mixture is stirred well. A suspension of 1M $CaHPO_4$ (10 $\mu$L) and a solution of 1.68M $\delta$-gluconolactone (40 $\mu$L) are thoroughly stirred into this mixture. The final mixture (0.2 mL) is cast on the inside of an eppendorf tube and left overnight at 4° C. to gel. After overnight storage of the gel in vitro release is conducted in 10 mM Tris buffer, pH 7.5. This cast ethyl ester alginate gel with 30 mol % degree of esterification exhibits less than 5% burst and sustained release showing 20% released in 1 day and 40% released in 2 days.

EXAMPLE 6

The following example shows the preparation of a protein drug (GCSF)-containing alginate benzyl ester (DE=30 mol %) gel: and the in vitro sustained release from this gel.

This example is performed in a similar manner that described in Example 5 except the ethyl ester is replaced by the benzyl ester alginate. The ester alginate gels within the overnight storage period. The benzyl ester alginate gel with 30% of degree of esterification exhibits less 5% burst and sustained release showing 40% released in 1 day and 80% released in 2 days.

EXAMPLE 7

This example shows the preparation of alginate ethyl ester beads.

The gel beads are prepared by adding dropwise a 2% ester alginate solutions into 100 mM calcium chloride solutions (distilled water or 1M Tris HCl pH 7.0 buffer). The formed beads are washed with distilled water or buffer. Beads are prepared using either 30% or 50% degree of esterification.

EXAMPLE 8

This example shows the preparation of Leptin-containing alginate ester beads.

The beads are prepared by adding dropwise a solution of 25 mg/mL Leptin in 2% ethyl ester alginate (Tris HCl, pH 8.7) into a solution of 100 mM calcium chloride and 25 mM zinc chloride. The beads are prepared using 30% degree of esterification. The beads demonstrate sustained leptin release in vitro.

EXAMPLE 9

This example shows the molecular weight breakdown (or degradation) of ester alginates in buffers at neutral physiological pH.

Alginate esters (1% solution) are dissolved in either phosphate buffer (0.1M sodium phosphate, pH 6.8) or 0.1M Tris buffer (pH 7.0) and incubated at 37° C. The molecular weight breakdown is determined by measuring the decrease in the solution viscosity (Brookfield, 25° C.) at selected time intervals. Unmodified sodium alginate is found to be relatively stable in that its viscosity decreased only 5% in 8 days (phosphate buffer); however with ethyl and benzyl esters of alginic acid (DE=30%) the viscosity drops 35% in 8 days in same buffer. The amount of degradation of esters of alginic acid is also dependent on the degree of esterification, e.g., with ethyl ester of lower degree of esterification (DE=15%) the viscosity decreases 25% in 8 days. Thus the molecular weight breakdown is directly related to the degree of esterification.

EXAMPLE 10

This example shows the in vivo degradation (or gradual disappearance) of alginate ester hydrogels without protein and hydrogels containing protein.

The ester alginate gels are prepared in a similar manner to that described in Example 3 but the final mixture is taken up in a syringe and allowed to gel in the syringe at 4° C. overnight. Then 100 $\mu$L of gel is injected subcutaneously into the back of the neck of mice (Charles River, 12 week old female, BDF1, 20 g, 5 mice per group) and the site surgically examined periodically on different members of the group.

Using ethyl and benzyl ester alginate material with DE=30%, the results of the single injection site study show that the ester alginate hydrogels disappear within 2 weeks. Using ethyl ester alginate gel with DE=15%, the gels are still present at 30 and 61 days, but reduced in size. Using ethyl ester alginate material with DE=5%, the gels are still present at 30 and 61 days with little reduction in size. Using the unsubstituted sodium alginate material, the gel persists relatively unchanged through day 61.

The rate of disappearance of the ester alginate gels is similar with or without protein.

EXAMPLE 11

This example provides weight loss and pharmacokinetics data for leptin-containing alginate ester hydrogels in rats.

The ethyl ester alginate gels are prepared in a similar manner to that described in Example 4 but the final mixture is taken up in a syringe and allowed to gel in the syringe at 4° C. overnight. Rats are given a bolus dose of 0 mg/kg (control) and 100 mg/kg, then blood levels and weight loss are monitored for seven days.

The results show: the ethyl ester alginate with DE=5 mol % exhibits a steady blood level of ~2000 ng/mL for 3 days, then declines to 2~3 ng/mL over the next 3–4 days; the ethyl ester alginate with DE=15 mol % exhibits a steady blood level of ~2000 ng/mL for 2 days, then declines to 2–3 ng/mL at 5 days; the ethyl ester alginate with DE=30 mol % exhibits a blood level of ~2000 ng/mL for 1 day, which decreases to 2–3 ng/mL at 4 days; the blood level of Zn-leptin suspention peaks at 12 hr, then decreases to 1–2 ng/mL at 6 days. All animals exhibit weight loss showing that the Zn-leptin is active. The results also show that incorporating Zn-leptin in the ethyl ester alginate gels (DE=5 mol % and 15 mol %) nearly doubles (factor of 1.8–1.9) the area under the curve (AUC) of the Zn-leptin, suggesting a doubling of the bioavailability; and use of ethyl ester alginate gel (DE=30 mol %) shows a similar bioavailability to Zn-leptin, based on AUC.

We claim:

1. A sustained-release delayed gel composition, comprising:
   a) a biodegradable anionic polysaccharide;
   b) a leptin protein and analogs or derivatives thereof; and
   c) at least one bound polyvalent metal ion, wherein said biodegradable anionic polysaccharide is an alginate ester which is crosslinked with said polyvalent metal ion to provide a biodegradable, biocompatible alginate ester hydrogel which is formed in a time-delayed manner, is injectable, and results in no injection site reaction.

2. The sustained-release composition of claim 1 wherein the bound polyvalent metal ion is a mixture of bound and unbound polyvalent metal ion.

3. The sustained-release delayed gel of claim 1 further comprising excipients for stabilizing the leptin or the hydrophilic polymer.

4. The composition of claim 1 wherein the bound polyvalent metal ion is a salt selected from the group consisting of acetates, phosphates, lactates, tartrates, citrates, chlorides, carbonates or hydroxides thereof.

5. The composition of claim 4 wherein the metal ion is selected from the group consisting of manganese, strontium, iron, magnesium, calcium, barium, copper, aluminum or zinc.

6. The composition of claim 5 wherein the metal ion is calcium.

7. The composition of claim 3 wherein the leptin consist of at least 0.001 mg/ml.

8. The composition of claim 1 wherein the leptin is a complexed leptin.

9. The composition of claim 8 wherein the complexed leptin is a precipitated leptin.

10. The composition of claim 9 wherein the precipitated leptin is a zinc leptin precipitate.

11. A pharmaceutical formulation comprising the sustained-release composition according to claims 1, 2, or 3 in a pharmaceutically acceptable carrier, diluent or adjuvant.

12. The pharmaceutical formulation of claim 11, wherein the formulation is in a syringe.

* * * * *

UNITED STATES PATENT AND TRADEMARK OFFICE
CERTIFICATE OF CORRECTION

PATENT NO. : 6,432,449 B1
DATED : August 13, 2002
INVENTOR(S) : Goldenberg et al.

It is certified that error appears in the above-identified patent and that said Letters Patent is hereby corrected as shown below:

Column 4,
Line 31, change "gent" to -- agent --.

Column 6,
Line 20, change "ccycloaliphatic" to -- cycloaliphatic --.

Column 7,
Line 66, change "mol %" to -- 15 mol % --.

Column 11,
Line 56, change "95/7206" to -- 95/17206 --.

Signed and Sealed this

Twenty-sixth Day of August, 2003

JAMES E. ROGAN
*Director of the United States Patent and Trademark Office*